US00PP26273P2

(12) United States Plant Patent
Hansen

(10) Patent No.: US PP26,273 P2
(45) Date of Patent: Dec. 22, 2015

(54) ***SALVIA* PLANT NAMED 'VIOLET RIOT'**

(50) Latin Name: ***Salvia* hybrid (Linnaeus)**
Varietal Denomination: Violet Riot

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 125 days.

(21) Appl. No.: 13/999,908

(22) Filed: Apr. 2, 2014

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Annette Para

(57) ABSTRACT

The new and distinct cultivar of perennial *Salvia* plant named 'Violet Riot' characterized by its large vivid violet-blue flowers with deep purple calyxes densely arranged in verticils, compact rounded habit with stiff, upright, branched stems and strong vigorous winter-hardy growth rate and gray-green foliage.

1 Drawing Sheet

Botanical denomination: *Salvia* hybrid (Linnaeus).
Cultivar designation: 'Violet Riot'.

BACKGROUND OF THE INVENTION

The present invention relates to a new and distinct cultivar of ornamental Sage plant hereinafter referred to by the cultivar name *Salvia* 'Violet Riot' or as the new plant. The new plant was discovered in the summer of 2012 by the inventor, Hans A. Hansen. *Salvia* 'Violet Riot' was the result of a chance seedling the residential perennial garden of the inventor in Zeeland, Mich., USA. The female (seed) parent and male (pollen) parent are both unknown. *Salvia* 'Violet Riot' was placed in comparison trials at a nursery in Zeeland, Mich., USA in the summer of 2013 and approved for introductions that year by the inventor, Hans A. Hansen. The plant was then further tested with asexual propagation by tip cuttings taken in 2012. The resulting plants of *Salvia* 'Violet Riot' asexually propagated at the same wholesale perennial nursery in Zeeland, Mich. have been found to be true to type and stable in successive generations.

SUMMARY OF THE INVENTION

Plants of *Salvia* 'Violet Riot' have not been observed under all possible environmental conditions. The phenotype may vary somewhat with variations in environment such as temperature, nutrition and light intensity, etc. without, however, any variance in genotype.

The nearest comparison cultivars are *Salvia* 'May Night' (not patented) and *Salvia* 'East Friesland' (not patented). *Salvia* 'Violet Riot' is more upright and slightly taller than 'May Night'. The flower color of 'May Night' is slightly more blue and 'Violet Riot' is more violet. 'East Friesland' flowers about a week later and is a little shorter, is less upright and is slightly more purple in flower than 'Violet Riot'.

The following characteristics in combination distinguish *Saliva* 'Violet Riot' as a new and distinct cultivar:

1. Large vivid violet-blue colored flowers with deep purple calyxes densely arranged in verticils from late spring into early summer;

2. Compact overall rounded habit with stiff, upright, branched stems;
3. Strong, vigorous and winter-hardy growth;
4. Rugose gray-green foliage.

BRIEF DESCRIPTION OF THE DRAWINGS

The photographs of the new plant demonstrate the unique traits and the overall appearance of *Salvia* 'Violet Riot'. The colors are as accurate as reasonably possible with color reproductions. Variation in ambient light spectrum, source and direction may cause the appearance of minor variation in color. The plant used in the photographs was a two-year old plant grown in an open, full-sun trial garden at a wholesale perennial nursery in Zeeland, Mich. with supplemental water and fertilizer when needed. No plant growth regulators have been used.

DETAILED BOTANICAL DESCRIPTION

Figure 1:
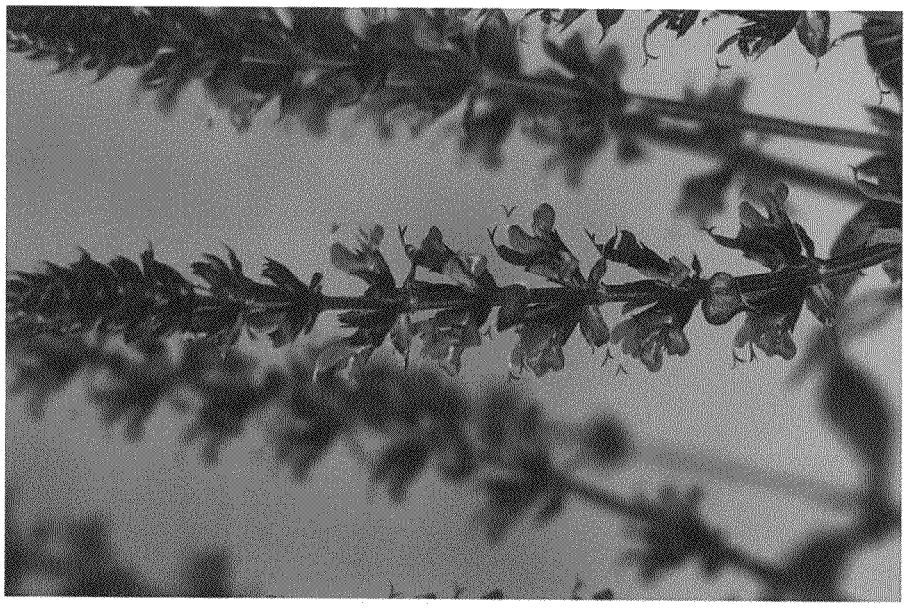
FIG. 1 shows a close-up of the flower scape with the buds, calyxes and vivid violet-blue petal color.
Figure 2:
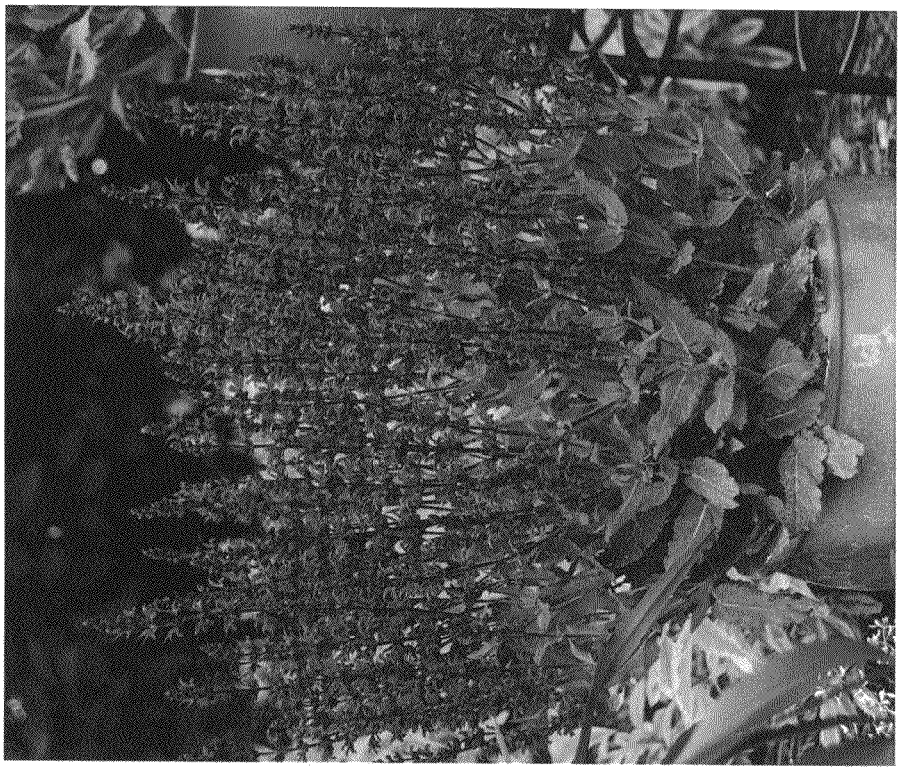
FIG. 2 shows the plant habit in full flower in a landscape.

The following descriptions and color references except where common dictionary terms are used are based on the 2001 edition of The Royal Horticultural Society Colour Chart. *Salvia* 'Violet Riot' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing in an outdoor full-sun trial garden at a wholesale perennial nursery in Zeeland, Mich. Plants were given supplemental water and fertilizer but no plant growth regulators were used.

Botanical classification: *Salvia nemorosa* (Linnaeus).

Parentage: Female or seed parent is unknown; unknown male or pollen parent.

Plant habit: Winter-hardy herbaceous perennial; multi-stemmed, with basal foliage largest and distally smaller opposite leaves at nodes, and flowers in several tightly arranged verticils on branched upright racemes displayed above foliage; in flower with panicles about 60 cm tall and about 60 cm wide at the fullest point; foliage extends up the stems to about two thirds the height of plant.

Propagation: By herbaceous tip cuttings; time to produce a rooted stems about two weeks.

Growth rate: Rapid, vigorous, finishing in a 65 mm container in about 7 weeks from rooted cutting, and from 65 mm container to flowering 3.8 liter container in about 8 weeks.

Root description: Fine, well-branched; color dependent on age and soil type, from cream to dark tan in color.

Foliage: Opposite, simple, rugose, lanceolate, glabrous upper and lower surfaces except veins; margin crenate; acute apex and base cordate to auriculate with lobes sometimes overlapping; lightly pubescent both surfaces; size to about 12.0 cm long; leaf blades about 9.0 cm long and 4.5 cm across, decreasing in size distally; average leaves with petiole about 10.0 cm long and 3.5 cm across; faint sage fragrance.

Foliage color: Adaxial surface between RHS 136B and RHS N138A; abaxial surface between RHS N138D and RHS N139C.

Venation: Reticulate; impressed on adaxial side and ridged on abaxial side; pubescent, more heavily on abaxial.

Vein color: Adaxial midrib lighter than RHS 138D and RHS 145D, main veins nearest RHS N138C and veinlets same color as surrounding tissue; abaxial midrib and main veins lighter than RHS 145D, veinlets beginning lighter than RHS 145D and becoming nearest RHS 138D toward leaf margin.

Petiole: Concave adaxial side, convex abaxial side, pubescent; to about 4.0 cm long and 5.0 mm wide, average 3.0 cm long and 4.0 mm wide at base.

Petiole color: Adaxial surfaces center nearest RHS 145D and margins between RHS 139B and RHS 139C; abaxial center lighter than RHS 145D and margins between RHS 139B and RHS 139C.

Flower description: Perfect, bilabiate, verticillate with flowering generally beginning at lower verticils and advancing up the scape; average distance between verticils about 8.0 mm, greater proximally and less distally; with lower lip projected at about 30 degree angle above horizontal and banner petal about 60 degree angle above horizontal; self-cleaning, petals not persistent; flowering beginning late spring for about four weeks and repeating if initial scapes removed.

Flower longevity: About four days on the plant or as cut flower.

Fragrance: Faint sweet honey.

Flower buds one to two days prior to anthesis: Shape is rounded on top and slightly concave below, with rounded apex; pubescent; about 7.0 mm long, 3.0 mm tall and 2.0 mm wide.

Bud color: Petals nearest RHS N187A; abaxial calyx distal region nearest RHS 187A, base nearest RHS138B with veins nearest RHS 187B; adaxial calyx base nearest RHS 144B with tinting of veins nearest RHS 187B, and proximal region nearest RHS 187B with darker veins of nearest RHS 187A.

Flowers: About 1.1 cm long, 8.0 mm tall and 4.0 mm wide; clustered at verticils with normally six flowers per verticil.

Petals: Bilabiate corolla; upper banner petal fused to lower labium; upper banner petal and flattened side to side vertically with notched apex, labium of four lobes with larger two fused to apex upturned concaved.

Banner (upper) petal: Pubescent outside and glabrous inside; about 1.1 cm long, 3.0 mm tall and 2.0 mm across.

Labium (lower petal): Pubescent outside and glabrous inside; consisting of four lobes; two flattened proximal lobes about 2.5 mm long and 1.0 mm wide at base with acute apex and fused to labium about 7.0 mm from base; two distal lobes fused into one forming upward facing cup about 1.5 mm deep with rounded apex, about 11.0 mm long 4.0 mm wide with rounded apex and no apical notch between.

Petal color: Upper banner petal nearest RHS N88A outside and between RHS N88B and RHS N88C inside; lower labium petal nearest RHS N88A in both inner and outer surfaces; fused base of petals lightening to near white, much lighter than RHS N155A.

Androecium: Two, fused with labium, contained within banner petal.

*Filament*.—Glabrous, fused about 6.0 mm from base of labium petal; curved around inside of banner petal; about 2.5 mm long rounded at point of anther attachment and less than 0.5 mm diameter, with flattened flared region at base point of fusion with banner petal about 1.0 nun across; color proximal region nearest RHS N88A, lightening to nearest RHS N88C before stamen.

*Anther*.—Glabrous, oblong, less than1.0 mm long and less than 0.5 mm diameter; longitudinal, dorsifixed; color nearest RHS N89A.

*Pollen*.—Globose, less than 0.5 mm circumference; color nearest RHS 11B.

Gynoecium: One, curved around inside of banner petal and protruding in distal 4.0 mm.

*Style*.—About 1.3 cm long and less than 1 mm diameter; color lighter than RHS 85D at base, darkening distally to nearest RHS 86B before stigma split.

*Stigma*.—Split in two and curved in the terminal 2.0 mm; apex pointed; color nearest RHS 86A.

*Ovary*.—Superior; color nearest RHS 144A.

*Fruit*.—Nutlet, up to four at base inside calyx; rounded, about 1.0 mm diameter; color darker than RHS 200A.

*Calyx*.—Five sepals, three upper and two lower, campanulate, apex acute; fused base; tube about 7.0 mm long and 4.0 mm tall at mouth and 2.0 mm wide; lower set fused to within 3.0 mm of apex and cleft about 3.0 mm deep between upper and lower set; upper set of three fused to about 0.5 mm of apex.

*Calyx color*.—Abaxial base nearest RHS 145B with distal tinting developing of between RHS N186C and RHS N187B; adaxial base nearest RHS 145B and distal one half darkening to nearest RHS 137B with tinting nearest RHS N186C; abaxial and adaxial veins of nearest RHS 141B with tinting of nearest RHS 186C developing distally.

Bracts: Each verticil subtended by two opposite bracts; apex acuminate, base attenuate, shape nearly cordate; margin minutely pubescent, and glabrous above and below; bract size up to 10.0 mm long and 7.0 mm wide, decreasing distally.

Bract color: Both surfaces between RHS 137A and RHS 137B on 1.0 to 2.0 mm wide margins and veins stretching about two thirds way to base, with translucent center and base between RHS 71A and RHS 71B.

Peduncles: Quadrangular in cross section; about 18 per plant; strong; mostly upright, up to 60 cm tall and 5.0 mm across; finely pubescent; branches upright at lower nodes with branches to about 25.0 cm long and 3.0 mm across; average internode distance about 7.0 cm.

Peduncle color: Between RHS 138A and RHS 138B in upper and lower regions with stippling of nearest RHS 187A concentrated in the upper regions and area receiving more light.

Pedicels: Cylindrical, about 3.0 mm long and 0.5 mm diameter; pubescent; held about 45 degrees above horizontal.

Pedicel color: Between RHS N186C and RHS N187B.

Disease and pest resistance: Plants of *Salvia* 'Violet Riot' perform best with adequate moisture and good drainage; are hardy from USDA zone 3 to 8; resistant to diseases and pests beyond that common to *Salvia* has not been noted.

It is claimed:

1. The new and distinct perennial *Salvia* plant named 'Violet Riot' as herein described and illustrated useful for landscaping as a specimen plant, en masse or as a cut flower.

* * * * *